United States Patent [19]

Charnley

[11] 4,324,006
[45] Apr. 13, 1982

[54] BLANK FOR ACETABULAR PROSTHESIS
[75] Inventor: John Charnley, Knutsford, England
[73] Assignee: Charnley Surgical Inventions Limited, England
[21] Appl. No.: 904,752
[22] Filed: May 11, 1978
[30] Foreign Application Priority Data May 30, 1977 [GB] United Kingdom ............... 30385/77

[51] Int. Cl.³ ............................................. A61F 1/03
[52] U.S. Cl. ........................................ 3/1.912; 3/1.9; 128/92 C
[58] Field of Search ...................... 3/1.912, 1.913, 1.9, 3/1.91, 1.911; 128/92 CA, 92 C

[56] References Cited
U.S. PATENT DOCUMENTS

| | | | |
|---|---|---|---|
| 2,947,308 | 8/1960 | Gorman | 3/1.912 X |
| 3,874,003 | 4/1975 | Moser et al. | 128/92 C X |
| 3,882,550 | 5/1975 | Karpf et al. | 128/92 C X |
| 3,986,212 | 10/1976 | Saver | 3/1.912 X |
| 4,059,854 | 11/1977 | Laure | 3/1.91 |
| 4,123,806 | 11/1978 | Amstutz et al. | 128/92 C X |

OTHER PUBLICATIONS

Vitallium Surgical Appliance Catalog, Austenal Medical Division, Howmet Corp., N.Y., N.Y.; p. 30; 1964.

*Primary Examiner*—Clifford D. Crowder
*Attorney, Agent, or Firm*—Ross, Ross & Flavin

[57] ABSTRACT

An acetabular prosthesis for use in an artificial hip joint. Because acetabula vary in size, it is not practicable to produce a single prosthesis for each acetabulum, being preferable to provide a blank which can be manually trimmed to fit each acetabulum. Here a blank is used in the formation of an acetabular prosthesis comprising a body surrounding and defining a part-spherical socket whose entrance is surrounded by an annular rim and having a flange extending outwardly and rearwardly from the periphery of the rim and made of a material capable of being manually trimmed to be asymmetrical. The flange may be marked with cutting lines to indicate where it should be trimmed to fit a left or right acetabulum.

3 Claims, 5 Drawing Figures

BLANK FOR ACETABULAR PROSTHESIS

This invention relates to an acetabular prosthesis for use in an artificial hip joint.

When an acetabular prosthesis is to be inserted into an acetabulum, the acetabulum is enlarged, by means of a reamer, to have a substantially hemispherical portion 10 and a part-cylindrical portion 11, as will be seen from FIG. 3 of the accompanying drawing. The reamer is rotated about the axis A—A. A known acetabular prosthesis, having a regular small flange, cannot be disposed in the acetabulum at the desired angle of 45°, i.e. with the axis of the socket on line B—B, and still have its rim in contact with the edges of the acetabulum. This has the effect that the prosthesis may tilt in the cement whilst it is soft causing poor adherence between the cement and the bone and prosthesis. Further, the gaps between the edge of the known prosthesis and the acetabulum allow cement to escape freely during insertion.

An object of the invention is to provide an improved acetabular prosthesis.

The invention provides an acetabular prosthesis in the form of a body surrounding and defining a part-spherical socket whose entrance is surrounded by an annular rim, an asymmetrical flange extending outwardly and rearwardly from the periphery of the rim.

The flange will normally be small in width around about 180° of the body of the prosthesis and then broaden out into a crescent shape around the remainder of the body. Advantageously the flange extends rearwardly of the said rim of the body, preferably at an angle of between 40° and 50°. The flange can be integrally moulded with the body or can be detachably fastened thereto. In the latter case the flange can be supplied in a variety of shapes to fit differently shaped acetabula. The flange can also, if separate, be of different material from the material of the body.

Because acetabula vary in size, it is not practicable to produce a single prosthesis for each acetabulum and it is preferable to provide a blank which can be manually trimmed to fit each acetabulum. Accordingly the invention also provides a blank for use in the formation of an acetabular prosthesis as claimed in any preceding claim, and comprising a body surrounding and defining a part-spherical socket whose entrance is surrounded by an annular rim and having a flange extending outwardly and rearwardly from the periphery of said rim and made of a material capable of being manually trimmed to be asymmetrical.

Preferably the flange is marked with cutting lines to indicate where it should be trimmed to fit a left or right acetabulum.

The invention will be described further, by way of example, with reference to the accompanying drawing, wherein.

Figure 1:
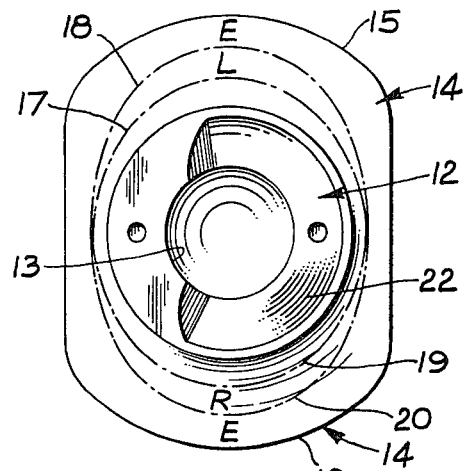
FIG. 1 is a front elevation of a preferred blank of the invention.
Figure 3:
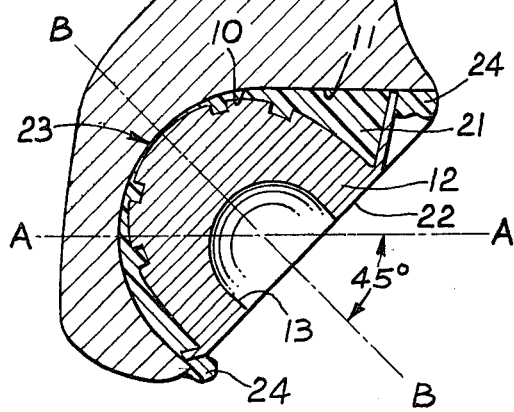
FIG. 3 is a cross section showing a preferred acetabular prosthesis of the invention (formed by trimming the blank of FIG. 1) in position in an acetabulum.

As will be seen from FIG. 1, a preferred blank of the invention comprises a body 12 totally surrounding and defining a part-spherical femoral-prosthesis-head receiving socket 13. The entrance to the socket 13 is surrounded by a rim 12 in the form of an annular face. Rearwardly and outwardly extending from the plane of the rim 12 is an integral semi-flexible flange 14 which is asymmetrical in that it is not of uniform width. It has two generally crescent shaped lobes 15, 16 marked with cutting lines 17, 18, 19, 20 and designations E and L and R and E. The body and flange are injection moulded from high density polyethylene. When the prosthesis is to be used in a right acetabulum the blank is trimmed along the line 19 and, provided the acetabulum is of normal shape, along line 18. This forms the prosthesis which is illustrated in FIG. 3. For a normal left acetabulum cutting occurs along lines 20 and 17. If the acetabulum should be larger than normal the cut on the wider side of the flange can be made between line 18 and 20 and the edge of the lobe 15 and 16 to include part of the extra area marked E.

Figure 2:
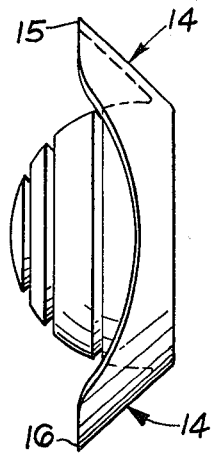
FIG. 2 is a side view of the blank of FIG. 1.
Figure 4:
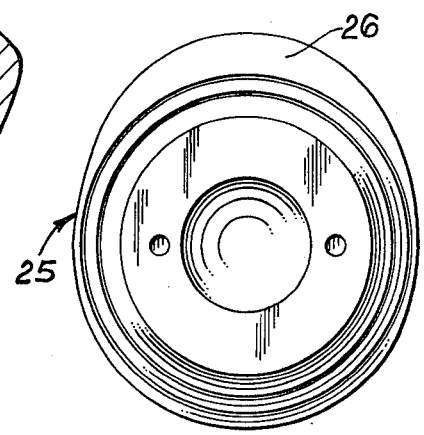
FIG. 4 is a front elevation of a second blank of the invention.
Figure 5:
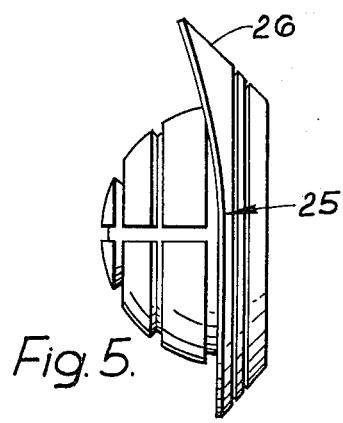
FIG. 5 is a side view of the blank of FIG. 4.

FIGS. 4 and 5 illustrate an acetabular prosthesis 25 which does not have the long posterior wall feature of the prosthesis of FIGS. 1, 2 and 3. Thus only a single lobe 26 on one side need be provided as the prosthesis 25 is symmetrical and can be used for left or right joints. The lobe 26 is illustrated after trimming, for example from the shape of lobe 15 or 16.

When the trimmed prosthesis, or prosthesis 25, is inserted into an acetabulum containing cement 21, the rearmost part of the body contacts the base of the acetabulum at 23 and the flange contacts the wall of the acetabulum all around the prosthesis. However, the fit is not a sealing fit (especially as the flange is preferably cut to have a serrated edge). This has two advantages: firstly, the contact between the flange and the wall of the acetabulum maintains the prosthesis firm against rocking in the acetabulum, which can cause separation between the cement and the body or the cement and the acetabulum; secondly, the flange substantially closes the acetabulum and applies a certain pressure to the cement to cause close contact between it and the body and acetabulum. The fit is not too close, however to prevent escape of excess cement which can pass through gaps between the flange and acetabulum wall as indicated at 24. Such excess cement 24 will normally be removed before it has set.

The invention is not limited to the precise details of the foregoing and variations can be made thereto. For example the rim can be removably attached to the body and can be of a material different from the material of the body.

What I claim is:

1. A blank for use in the formation of an acetabular prosthesis and comprising: a body having a blind part-spherical socket, an annular rim surrounding the socket entrance and having a flange extending outwardly of and rearwardly from the rim periphery, the flange being marked with cutting lines for the trimming of same to a non-uniform width.

2. A blank as claimed in claim 1, wherein the flange is in the form of two diametrically opposite lobes.

3. A blank as claimed in claim 2, wherein each lobe is marked with cutting lines.

* * * * *